United States Patent [19]

Dunn et al.

[11] 4,133,882
[45] * Jan. 9, 1979

[54] 7-HYDROXYHALOPHENYLACETAMIDO-3-HETEROCYCLICTHIOMETHYL CEPHALOSPORINS

[75] Inventors: George L. Dunn, Wayne; John R. E. Hoover, Glenside, both of Pa.

[73] Assignee: SmithKline Corporation, Philadelphia, Pa.

[*] Notice: The portion of the term of this patent subsequent to Feb. 18, 1992, has been disclaimed.

[21] Appl. No.: 700,668

[22] Filed: Jun. 28, 1976

Related U.S. Application Data

[63] Continuation of Ser. No. 359,567, May 11, 1973, abandoned, which is a continuation-in-part of Ser. No. 262,903, Jun. 14, 1972, Pat. No. 3,867,380, which is a continuation-in-part of Ser. No. 116,598, Feb. 18, 1971, abandoned, which is a continuation-in-part of Ser. No. 99,296, Dec. 17, 1970, abandoned, and a continuation-in-part of Ser. No. 289,499, Sep. 15, 1972, Pat. No. 3,855,213, which is a continuation-in-part of Ser. No. 262,903, , and Ser. No. 116,599, Feb. 18, 1971, abandoned, which is a continuation-in-part of Ser. No. 99,296.

[51] Int. Cl.² .................. A61K 31/545; C07D 501/36
[52] U.S. Cl. ........................................ 424/246; 544/26
[58] Field of Search .................... 260/243 C; 424/246; 544/26

[56] References Cited

U.S. PATENT DOCUMENTS

| 3,157,648 | 11/1964 | Collins | 260/243 C |
|---|---|---|---|
| 3,167,549 | 1/1965 | Hoover | 260/243 C |
| 3,489,751 | 1/1970 | Crast | 544/30 |
| 3,516,997 | 6/1960 | Tokano et al. | 260/243 C |
| 3,634,418 | 1/1972 | Willner et al. | 424/246 |
| 3,867,380 | 2/1975 | Dunn et al. | 260/243 C |

Primary Examiner—Donald G. Daus
Assistant Examiner—David E. Wheeler
Attorney, Agent, or Firm—Stuart R. Suter; Alan D. Lourie; William H. Edgerton

[57] ABSTRACT

Cephalosporin compounds substituted in the 7-position with a hydroxy-halo substituted α-aminophenylacetamido group and in the 3-position with a heterocyclicthiomethyl group are prepared by 7-acylation. The products are antibacterial agents.

11 Claims, No Drawings

7-HYDROXYHALOPHENYLACETAMIDO-3-HETEROCYCLICTHIOMETHYL CEPHALOSPORINS

This is a continuation of application Ser. No. 359,567 filed May 11, 1973, now abandoned, which is a continuation-in-part of copending application Ser. No. 262,903, filed June 14, 1972, now U.S. Pat. 3,867,380 which was a continuation-in-part of application Ser. No. 116,598, filed Feb. 18, 1971, now abandoned, which was a continuation-in-part of application Ser. No. 99,296, filed Dec. 17, 1970, now abandoned, and it is also a continuation-in-part of copending application Ser. No. 289,499, filed Sept. 15, 1972, now U.S. Pat. 3,855,213 which is a continuation-in-part of copending application Ser. No. 262,903, filed June 14, 1972 now U.S. Pat. 3,867,380 and of application Ser. No. 116,599, filed Feb. 18, 1971, now abandoned, which latter application was a continuation-in-part of application Ser. No. 99,296 filed Dec. 17, 1970, now abandoned.

This invention relates to chemical compounds known as cephalosporins, which compounds possess antibacterial activity.

The compounds of this invention are represented by the following structural formula:

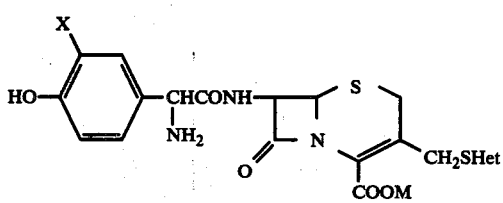

in which:

M is hydrogen or an alkali metal or ammonium cation
X is fluoro, chloro or bromo; and
Het is a five or six membered heterocyclic ring containing carbon and one to four atoms selected from the group consisting of N, O and S, unsubstituted or substituted with from one to two groups selected from lower alkyl, lower alkoxy or alkoxyalkyl, each alkoxy or alkyl having from one to four carbon atoms, trifluoromethyl, hydroxy, hydroxymethyl, halogen, and SR, with R being hydrogen or lower alkyl of from one to four carbon atoms.

Preferred compounds are those where Het is unsubstituted or substituted 1,2,3-triazolyl, 1,2,4-triazolyl, 1,2,3,4-tetrazolyl, oxazolyl, thiazolyl, 1,3,4-oxadiazolyl, 1,3,4-thiadiazolyl or 1,2,4-thiadiazolyl. Also preferred are those compounds where X is fluoro or chloro.

It is also recognized that when the substituent on the heterocyclic group is hydroxy or mercapto, it is possible for the substituent to exist in another tautomeric form, i.e. the oxo or thiono form. The compound may exist exclusively as one of the two tautomers or may be in equilibrium between the two; however, these are all included within the scope of this invention.

Cephalosporin derivatives substituted in the 7-position with a phenylglycylacetamido side chain are well documented in the prior art. Examples of hydroxy-chloro disubstitution on the phenyl moiety are found in U.S. Pat. Nos. 3,634,418, 3,579,514 and 3,489,751. None of the above cited references discloses a hydroxy-fluoro compound or any hydroxy-halo compound with a heterocyclic thiomethyl group at position 3 of the cephem nucleus.

Variously substituted, including hydroxy-chloro aromatic α-amino acids are described in Belgian Pat. No. 774029 and Netherlands Pat. No. 71,06054. However, 4-hydroxy-2-or 3-fluorophenylglycines are not disclosed.

The compounds of this invention are prepared by acylation of the appropriate 7-amino-3-heterocyclicthiomethyl cephalosporin nucleus with a suitably substituted phenylglycine. Prior to acylation, it is desirable to protect the amino group of the glycine moiety with an easily removable protective group such as t-butoxycarbonyl, benzyloxycarbonyl, trichloroethoxycarbonyl, or similar protective group commonly used in the synthesis of peptides. The carboxyl group can be activated for acylation by conversion to the acid chloride or to a mixed anhydride with, for example, a lower alkyl chloroformate. It can also be activated by conversion to the 2,4-dinitrophenyl or N-hydroxysuccinimidyl esters. If an ester of the carboxyl group on the cephalosporin nucleus is used as an acylation substrate, e.g., a benzhydryl, t-butyl, trichloroethyl, or benzyl ester, the amine-protected phenylglycine can be coupled directly to the 7-amino group by using a carbodiimide such as dicyclohexylcarbodiimide. Alternatively, the protected phenylglycine can be activated for condensation by reacting it first with carbonyl diimidaziole or its equivalent.

Following the acylation, the protective groups can be removed with an acid such as trifluoroacetic acid. The resulting salt is converted to the zwitterionic product by means of a basic ion exchange resin such as polystyrene-amine ion exchange resin (Amberlite IR-45) or else by basification of an aqueous solution of the salt.

The compounds are also prepared by displacement of a 7-acylated 3-acetoxymethylcephalosporin with a mercaptoheterocycle in an aqueous, slightly basic medium.

The substituted phenylglycyl starting materials are prepared from halophenols by known methods (Belgian Pat. No. 774029). The 7-amino-3-heterocyclicthiomethyl cephalosporin nuclei are prepared by methods disclosed in the prior art from 7-aminocephalosporanic acid (7-ACA) and the appropriate heterocyclic mercaptan compound.

The compounds described in this invention have antibacterial activity against both Gram-positive and Gram-negative organisms. Minimum inhibitory concentrations (MIC) ranged from 1.6 to 100 μg./ml in in vitro testing. These results are shown below for 7-[DL-α-amino-α-(3-fluoro-4-hydroxyphenyl)acetamido]-3-(2-methyl-1,3,4-thiadiazol-5-ylthiomethyl)-3-cephem-4-carboxylic acid (I), 7-[DL-α-amino-α-(3-fluoro-4-hydroxyphenyl)acetamido]-3-(1-methyl-1,2,3,4-tetrazol-5-ylthiomethyl)-3-cephem-4-carboxylic acid (II), 7-[DL-α-amino-α-(3-fluoro-4-hydroxyphenyl) acetamido]-3-(1,2,3-triazol-4-ylthiomethyl)-3-cephem-4-carboxylic acid (III), and 7-[DL-α-amino-α-(3-chloro-4-hydroxyphenyl)acetamido]-3-(1-methyl-1,2,3,4-tetrazol-5-ylthiomethyl)-3-cephem-4-carboxylic acid (IV). In vivo mouse protecting data are given in Table 2.

These compounds are formulated and administered orally and by injection in the same manner as other cephalosporins. Dosage is dependent upon the age and weight of the subject and on the infection being treated and can be determined by those skilled in the art based on the data disclosed herein and experience with known cephalosporins.

TABLE 1

| Bacteria | MIC (μg./ml.) in vitro | | | |
|---|---|---|---|---|
| | I | II | III | IV |
| S. aureus HH 127 | 6 | 6 | 3.1 | 6 |
| S. aureus SK 23390 | 6 | 6 | 3.1 | 6 |
| S. Villaluz | 50 | 50 | 50 | 25 |
| Strep. faecalis HH 34358 | 50 | 100 | 50 | 50 |
| E. coli SK 12140 | 25 | 6 | 6.3 | 6 |
| E. coli HH 33779 | 25 | 6 | 25 | 12 |
| Kleb. pneumo. SK 4200 | 13 | 3 | 3.1 | 3 |
| Kleb. pneumo. SK 1200 | 25 | 6 | 3.1 | 6 |
| Sal. paratyphi ATCC 12176 | 6 | 1.6 | 6.3 | 3 |
| Shig. paradys HH 117 | 13 | 3 | 3.1 | 1.6 |
| Entero. aerogenes ATCC 13048 | 25 | 13 | 25 | 12 |

TABLE II

| | ED$_{50}$ (mg./kg.) | | | |
|---|---|---|---|---|
| | E. coli 12140 | | Kleb. pneumo. 4200 | |
| Compound | s.c. | p.o. | s.c. | p.o. |
| II | <0.78 | 3.5 | 0.78 | 3.1 |
| III | 1.8 | 1.6 | <3 | <12 |
| IV | <3,1.7 | 6.2,5.5 | 3.5,3.5 | <12.5,6.2 |

It will be recognized that due to the asymmetric α-carbon atom in the 7-acetamido group, optical isomers will exist. Racemic or resolved products are obtained depending upon whether a racemic or resolved phenylglycine side chain is used. The resolved side chain acids are readily obtained from the racemic compounds by resolution according to well known methods including fractional crystallization of a salt formed with an optically active acid or base. Both the resolved and racemic products obtained from these side chain acids are within the scope of this invention.

Due to the presence of both an amine group and a carboxylic acid group in the cephalosporin compounds of this invention, it is possible, by standard methods, to prepare both acid and base salts of pharmaceutically acceptable nontoxic acids and bases as well as the zwitterionic forms of the compounds. Salts, when obtained, are readily converted to the zwitterions by known methods. It is to be understood that these salts are included in the scope of this invention.

The following examples illustrate the invention but are not to be construed as limiting the scope thereof. Temperatures are in degrees Centigrade unless otherwise stated.

EXAMPLE 1

7-Amino-3-(1-methyl-1,2,3,4-tetrazol-5-ylthiomethyl)-3-cephem-4-carboxylic acid

To a suspension of 27.2 g. (0.1 mol.) of 7-ACA in 200 ml. of water and 100 ml. of acetone was added a solution of 18.9 g. of sodium bicarbonate in 200 ml. of water. The resultant solution was warmed on a stream bath and a solution of 14.5 g. (0.125 mol.) of 1-methyl-5-mercapto-1,2,3,4-tetrazole in 200 ml. of acetone was added. The reaction mixture was refluxed for 3.5 hr. while maintaining the pH at 7.4–8.0 by addition of 5% sodium bicarbonate solution. Acidification of the cooled reaction mixture to pH 3.5 with 6N hydrochloric acid resulted in precipitation of 7-amino-3-(1-methyl-1,2,3,4-tetrazol-5-ylthiomethyl)-3-cephem-4-carboxylic acid which was collected, washed (H$_2$O) and air dried (16 g.; 49%).

EXAMPLE 2

When the appropriate heterocyclic mercaptan compound is substituted in the procedure of Example 1 for 1-methyl-5-mercapto-1,2,3,4-tetrazole the corresponding 7-amino-3-heterocyclicthiomethyl-3-cephem-4-carboxylic acid listed below is obtained.

7-amino-3-(5-methyl-1,3,4-thiadiazol-2-ylthiomethyl)-3-cephem-4-carboxylic acid 7-amino-3-(1,3,4-thiadiazol-2-ylthiomethyl)-3-cephem-4-carboxylic acid 7-amino-3-(5-ethyl-1,3,4-thiadiazol-2-ylthiomethyl)-3-cephem-4-carboxylic acid 7-amino-3-(5-trifluoromethyl-1,3,4-thiadiazol-2-ylthiomethyl)-3-cephem-4-carboxylic acid 7-amino-3-(5-n-butyl-1,3,4-thiadiazol-2-ylthiomethyl)-3-cephem-4-carboxylic acid 7-amino-3-(3-methyl-1,2,4-thiadiazol-5-ylthiomethyl)-3-cephem-4-carboxylic acid 7-amino-3-(3-ethyl-1,2,4-thiadiazol-5-ylthiomethyl)-3-cephem-4-carboxylic acid 7-amino-3-(thiazol-5-ylthiomethyl)-3-cephem-4-carboxylic acid 7-amino-3-(2-methylthiazol-5-ylthiomethyl)-3-cephem-4-carboxylic acid 7-amino-3-(4-methylthiazol-5-ylthiomethyl)-3-cephem-4-carboxylic acid 7-amino-3-(2,4-dimethylthiazol-5-ylthiomethyl)-3-cephem-4-carboxylic acid 7-amino-3-(1,3,4-oxadiazol-2-ylthiomethyl)-3-cephem-4-carboxylic acid 7-amino-3-(5-methyl-1,3,4-oxadiazol-2-ylthiomethyl)-3-cephem-4-carboxylic acid 7-amino-3-(oxazol-5-ylthiomethyl)-3-cephem-4-carboxylic acid 7-amino-3-(2-methyloxazol-5-ylthiomethyl)-3-cephem-4-carboxylic acid 7-amino-3-(4-methyloxazol-5-ylthiomethyl)-3-cephem-4-carboxylic acid 7-amino-3-(2,4-dimethyloxazol-5-ylthiomethyl)-3-cephem-4-carboxylic acid 7-amino-3-(1,2,3,4-tetrazol-5-ylthiomethyl)-3-cephem-4-carboxylic acid 7-amino-3-(1-ethyl-1,2,3,4-tetrazol-5-ylthiomethyl)-3-cephem-4-carboxylic acid 7-amino-3-(1-methoxymethyl-1,2,3,4-tetrazol-5-ylthiomethyl)-3-cephem-4-carboxylic acid 7-amino-3-(5-hydroxymethyl-1,3,4-oxadiazol-2-ylthiomethyl)-3-cephem-4-carboxylic acid 7-amino-3-(1,2,4-triazol-3-ylthiomethyl)-3-cephem-4-carboxylic acid 7-amino-3-(4-methyl-1,2,4-triazol-3-ylthiomethyl)-3-cephem-4-carboxylic acid 7-amino-3-(5-methyl-1,2,4-triazol-3-ylthiomethyl)-3-cephem-4-carboxylic acid 7-amino-3-(1-methyl-1,2,4-triazol-5-ylthiomethyl)-3-cephem-4-carboxylic acid 7-amino-3-(1-methyl-1,2,4-triazol-3-ylthiomethyl)-3-cephem-4-carboxylic acid 7-amino-3-(1,5-dimethyl-1,2,4-triazol-3-ylthiomethyl)-3-cephem-4-carboxylic acid 7-amino-3-(1,3-dimethyl-1,2,4-triazol-5-ylthiomethyl)-3-cephem-4-carboxylic acid 7-amino-3-(4,5-dimethyl-1,2,4-triazol-3-ylthiomethyl)-3-cephem-4-carboxylic acid 7-amino-3-(5-mercapto-1,2,4-triazol-3-ylthiomethyl)-3-cephem-4-carboxylic acid 7-amino-3-(5-methylthio-1,2,4-triazol-3-ylthiomethyl)-3-cephem-4-carboxylic acid 7-amino-3-(5-methoxymethyl-1,2,4-triazol-3-ylthiomethyl)-3-cephem-4-carboxylic acid 7-amino-3-(5-hydroxy-1,2,4-triazol-3-ylthiomethyl)-3-cephem-4-carboxylic acid 7-amino-3-(4-methyl-5-trifluoromethyl-1,2,4-triazol-3-ylthiomethyl)-3-cephem-4-carboxylic acid 7-amino-3-(4-allyl-1,2,4-triazol-3-ylthiomethyl)-3-cephem-4-carboxylic acid 7-amino-3-(5-hydroxy-4-methyl-1,2,4-triazol-3-ylthiomethyl)-3-cephem-4-carboxylic acid 7-amino-3-(4-ethyl-5-hydroxy-1,2,4-triazol-3-ylthiomethyl)-3-cephem-4-carboxylic acid 7-amino-3-(1-methyl-1,2,3-triazol-5-ylthiomethyl)-3-cephem-4-carboxylic acid 7-amino-3-(4-methyl-1,2,3-triazol-5-ylthiomethyl)-3-cephem-4-carboxylic acid 7-amino-3-(1,2,3-triazol-4-ylthiomethyl)-3-cephem-4-carboxylic acid.

7-amino-3-(5-mercapto-1,2,3-triazol-4-ylthiomethyl)-3-cephem-4-carboxylic acid 7-amino-3-(5-methylthio-1,2,3-triazol-4-ylthiomethyl)-3-cephem-4-carboxylic acid 7-amino-3-(5-methoxymethyl-1,2,3-triazol-4-ylthiomethyl)-3-cephem-4-carboxylic acid 7-amino-3-(5-hydroxy-1,2,3-triazol-4-ylthiomethyl)-3-cephem-4-carboxylic acid 7-amino-3-(4-pyridylthiomethyl)-3-cephem-4-carboxylic acid 7-amino-3-(3-pyridylthiomethyl)-3-cephem-4-carboxylic acid 7-amino-3-(4-pyrimidylthiomethyl)-3-cephem-4-carboxylic acid 7-amino-3-(2-pyrazinylthiomethyl)-3-cephem-4-carboxylic acid

EXAMPLE 3

N-t-Butoxycarbonyl-3-fluoro-4-hydroxyphenylglycine

To a suspension of 16.7 g. (0.09 mol.) of 3-fluoro-4-hydroxyphenylglycine and 7.2 g. (0.18 mol.) of magnesium oxide in 200 ml. of water maintained at 40–50° was added over a 15 minute interval 11.5 g. (0.09mol.) of t-butoxycarbonyl azide. The reaction mixture was stirred at 40–50° for 12 hr., then it was poured into 1.5 l. of water and the solution was extracted with ethyl acetate. The remaining aqueous phase was acidified to pH 2 with 40% phosphoric acid and extracted thrice more with ethyl acetate. The combined extracts were washed (H₂O), dried (MgSO₄) and concentrated to give 19 g. (74%) of N-t-butoxycarbonyl-3-fluoro-4-hydroxyphenylglycine.

EXAMPLE 4

N-t-Butoxycarbonyl-3-chloro-4-hydroxyphenylglycine

When 3-chloro-4-hydroxyphenylglycine is substituted in the procedure of Example 4 for 3-fluoro-4-hydroxyphenylglycine, the title compound is obtained.

EXAMPLE 5

N-t-Butoxycarbonyl-3-bromo-4-hydroxyphenylglycine

When 3-bromo-4-hydroxyphenylglycine is substituted in the procedure of Example 4 for 3-fluoro-4-hydroxyphenylglycine, the title compound is obtained.

EXAMPLE 6

7-]DL-α-amino-α-(3-fluoro-4-hydroxyphenyl)acetamido]-3-(5-methyl-1,3,4-thiadiazol-2-ylthiomethyl)-3-cephem-4-carboxylic acid To a cooled (0°) solution of 3.29 g. (0.010 mol.) of N-t-butoxycarbonyl-3-fluoro-4hydroxyphenylglycine in 60 ml. of dry tetrahydrofuran contained in a 250 ml. three-necked flask fitted with a thermometer and drying tube was added 1.52 ml. (0.011 mol.) of triethylamine. The reaction mixture was then cooled to −15° and 1.32 ml. (0.010 mol.) of isobutyl chloroformate was added with vigorous stirring over a 10 minute period. Stirring was continued for 20 minutes at −10° then a cold solution of 3.44 g (0.010 mol.) of 7-amino-3-(5-methyl-1,3,4-thiadiazol-2-ylthiomethyl)-3-cephem-4-carboxylic acid in 50 ml. of 50% aqueous tetrahydrofuran containing 1.52 ml. (0.011 mol.) of triethylamine was added over a 30 minute period. The reaction mixture was warmed to 5° and stirred for 1 hr., then stirred at 25° for an addition 1.5 hr. Evaporation of the solvent yielded a yellow residue which was dissolved in 100 ml. of water and 100 ml. of ethyl acetate. Triethylamine was added until pH 7.4, then the layers were separated and the aqueous phase was washed with ethyl acetate. The aqueous portion was cooled, 150 ml. of ethyl acetate was added and the mixture was acidified (pH 3.4) with 3N HCl. The layers were separated and the aqueous phase was again extracted with ethyl acetate. The combined extracts were washed (H₂O), dried (MgSO₄) and concentrated to give the title compound as a foam. The crude product was purified by chromatography on silica gel with CHCl₃—iPrOH—HCO₂H (90:10:3). Deblocking was accomplished by stirring the acid with 5 ml. of trifluoroacetic acid and 2.5 ml. of anisole at 25° for 30 minutes. Concentration and trituration of the residue with ether gave the salt as a yellow solid.

| $C_{18}H_{18}FN_5O_5S_3 \cdot CF_3COOH \cdot \tfrac{1}{2} H_2O \cdot \tfrac{1}{2} (C_2H_5)_2O$ | | |
|---|---|---|
| | Theory | Found |
| C | 40.74 | 40.76 |
| H | 3.42 | 3.35 |
| N | 10.80 | 10.39 |

The trifluoroacetate salt is converted to the zwitterion by stirring an aqueous solution of the salt with a polystyrene-amine ion-exchange resin (Amberlite IR-45) for one hour at 25°. The resin is then filtered off and the aqueous solution is lyophilized to yield the zwitterionic cephalosporin which may be converted to the sodium salt by addition of a 30% solution of sodium 2-ethylhexanoate in isopropanol.

EXAMPLE 7

7-[DL-α-amino-α-(3-fluoro-4-hydroxyphenyl)acetamido]-3-(1-methyl-1,2,3,4-tetrazol-5-ylthiomethyl)-3-cephem-4-carboxylic acid.

The title compound was obtained from reaction of 3.29 g. (0.010 mol.) of N-t-butoxycarbonyl-3-fluoro-4-hydroxyphenylglycine, 1.37 g. (1.32 ml.; 0.011 mol.) of isobutyl chloroformate and 3.28 g. (0.010 mol.) of 7-amino-3-(1-methyl-1,2,3,4-tetrazol-5-ylthiomethyl)-3-cephem-4-carboxylic acid by the procedure described in Example 6. Deblocking and salt formation were accomplished by stirring a solution of 0.4 g. of the protected amine in 4 ml. of trifluoroacetic acid and 4 ml. of m-dimethoxybenzene at 0°, then at 25° for 1 hr. Conversion to the zwitterion is accomplished as described in Example 6.

| $C_{18}H_{18}FN_7O_5S_2 \cdot CF_3COOH \cdot \frac{1}{4}(C_2H_5)_2O$ (628.091) | | |
|---|---|---|
| | Theory | Found |
| C | 40.10 | 40.76 |
| H | 3.45 | 3.68 |
| N | 15.60 | 15.73 |

EXAMPLE 8

7-[DL-α-amino-α-(3-fluoro-4-hydroxyphenyl)acetamido]-3-(1,2,3-triazol-4-ylthiomethyl)-3-cephem-4-carboxylic acid The title compound was obtained from reaction of 0.010 mol. of N-t-butoxycarbonyl-3-fluoro-4-hydroxyphenylglycine, 0.011 mol. of isobutyl chloroformate and 0.010 mol. of 7-amino-3-(1,2,3-triazol-4-ylthiomethyl)-3-cephem-4-carboxylic acid by the procedure described in Example 6.

| $C_{18}H_{17}FN_6O_5S_2 \cdot 1.75 H_2O$ (512.042) | | |
|---|---|---|
| | Theory | Found |
| C | 42.22 | 41.99 |
| H | 4.04 | 3.69 |
| N | 16.41 | 16.10 |

EXAMPLE 9

7-[DL-α-amino-α-(3-chloro-4-hydroxyphenyl)acetamido]-3-(1-methyl-1,2,3,4-tetrazol-5-ythiomethyl)-3-cephem-4-carboxylic acid To a solution of 1.15 g. (0.003 mol.) of 7-amino-3-(1-methyl-1,2,3,4,-tetrazol-5-ylthiomethyl)-3-cephem-4-carboxylic acid t-butyl ester and 1.35 g. (0.0035 mol.) of N-t-butoxycarbonyl-3-chloro-4-hydroxyphenylglycine in 50 ml. of dry tetrahydrofuran was added 0.72 g. (0.0035 mol.) of dicyclohexylcarbodiimide. The reaction mixture was stirred at 25° for 3 hr., then it was filtered and the filtrate was concentrated and absorbed onto 8 g. of silica gel. The crude product was chromatographed on 150 g. of silica gel with chloroform-methanol (99:1) to give 0.73 g. (37%) of pure compound. Deblocking was accomplished by stirring the intermediate with 3 ml. of trifluoroactic acid and 2 ml. of m-di-methoxybenzene at 25° for 1.5 hr. The reaction mixture was concentrated in vacuo to give the title compound salt as a residue which crystallized when triturated with ether.

| $C_{18}H_{18}ClN_7O_5S_2 \cdot CF_3COOH$ (628.823) | | |
|---|---|---|
| | Theory | Found |
| C | 38.58 | 39.39 |
| H | 3.11 | 3.43 |
| N | 15.59 | 15.49 |

When an equivalent amount of N-t-butoxycarbonyl-3-chloro-4-hydroxyphenylglycine is substituted into the procedure of Example 6 for N-t-butoxycarbonyl-3-fluoro-4-hydroxy-phenylglycine, 7-[DL-α-amino-α-(3-chloro-4-hydroxyphenyl)-acetamido]-3-(5-methyl-1,3,4-thiadiazol-2ylthiomethyl)-3-cephem-4-carboxylic acid is obtained.

In like manner, 7-[DL-α-amino-α-(3-fluoro-4-hydroxyphenyl)-acetamido]-3-(5-hydroxymethyl-1,3,4-oxadiazol-2-ylthiomethyl)-3-cephem-4-carboxylic acid is obtained from substitution of an equivalent amount of 7-amino-3-(5-hydroxymethyl-1,3,4-oxadiazol-2-ylthiomethyl)-3-cephem-4-carboxylic acid for 7-amino-3-(5-methyl-1,3,4-thiadiazol-2-ylthiomethyl) -3-cephem-4-carboxylic acid in the procedure of Example 6.

EXAMPLE 11

When an equivalent amount of N-t-butoxycarbonyl-3-bromo-4-hydroxyphenylglycine is substituted in the procedure of Example 9 for N-t-butoxycarbonyl-3-chloro-4-hydroxyphenyl-glycine or in the procedure of Example 7 for N-t-butoxycarbonyl-3-fluoro-4-hydroxyphenylglycine, 7-[DL-α-amino-α-(3-bromo-4-hydroxyphenylacetamido]-3-(1-methyl-1,2,3,4-tetrazol-5-ylthiomethyl)-3-cephem-4-carboxylic acid is obtained.

EXAMPLE 12

When an equivalent amount of N-t-butoxycarbonyl-3-chloro-4-hydroxyphenylglycine is substituted into the procedure of Example 8 for N-t-butoxycarbonyl-3-fluoro-4-hydroxyphenylglycine, 7-[DL-α-amino-α-(3-chloro-4-hydroxyphenyl)acetamido]-3-(1,2,3-triazol-4-ylthiomethyl)-3-cephem-4-carboxylic acid is obtained.

In the same manner, 7-[DL-α-amino-α-(3-bromo-4- hydroxphenyl) acetamido]-3- (1,2,3-triazol-4-ylthiomethyl) -3-cephem-4-carboxylic acid is obtained by substitution of an equivalent amount of N-t-butoxycarbonyl-3-bromo-4-hydroxyphenylglycine for N-t-butoxycarbonyl-3-fluoro-4-hydroxyphenylglycine in the procedure of Example 8.

EXAMPLE 13

When an equivalent amount of a 7-amino-3-heterocyclicthiomethyl-3-cephem-4-carboxylic acid listed in Example 2 is substituted into the procedure of Example 6 for 7-amino-3-(5-methyl-1,3,4-thiadiazol-2-ylthiomethyl)-3-cephem-4-carboxylic acid, the corresponding 7-[DL-α-amino-α-(3-fluoro-4-hydroxyphenyl)acetamido]-3-heterocyclicthiomethyl-3-cephem-4-carboxylic acid is obtained.

EXAMPLE 14

When equivalent amounts of a 7-amino-3-heterocyclicthiomethyl-3-cephem-4-carboxylic acid listed in Example 2 and of N-t-butoxycarbonyl-3-chloro-4-hydroxyphenylglycine are substituted into the procedures of Example 6, the corresponding 7-[DL-α-amino-α-(3-chloro-4-hydroxyphenyl)acetamido]-3-heterocyclicthiomethyl-3-cephem-4-carboxylic acid is obtained.

EXAMPLE 15

When equivalent amounts of a 7-amino- 3-heterocyclicthiomethyl-3-cephem-4 carboxylic acid listed in Example 2 and of N-t-butoxycarbonyl-3-bromo-4-hydroxyphenylglycine are substitute into the procedure of Example 6, the corresponding 7-[DL-α-amino-α-(3-bromo-4-hydroxyphenyl)acetamido]-3-heterocyclicthiomethyl-3-cephem-4-carboxylic acid is obtained.

EXAMPLE 16

An injectable pharmaceutical composition is formed by adding sterile water or sterile saline solution (2ml.) to 500 mg. of 7-[DL-α-amino-α-(3-fluoro-4-hydroxyphenyl)-acetamido]-3-(1-methyl-1,2,3,4-tetrazol-5-ylthiomethyl)-3-cephem-4-carboxylic acid, sodium salt.

Pharmaceutical compositions of the other antibacterial compounds disclosed above may be formulated in a similar manner.

EXAMPLE 17

A tablet or capsule is formed from 500 mg. of 7-[DL-α-amino-α-(3-fluoro-4-hydroxyphenyl)acetamido]-3-(1-methyl-1,2,3,4-tetrazol-5-ylthiomethyl)-3-cephem-4-carboxylic acid, 250 mg. of lactose and 75 mg. of magnesium stearate.

Tablets or capsules of the other antibacterial compounds disclosed above may be formulated in a similar manner, particularly using the compounds of Examples 8 and 9.

We claim:

1. A compound of the formula

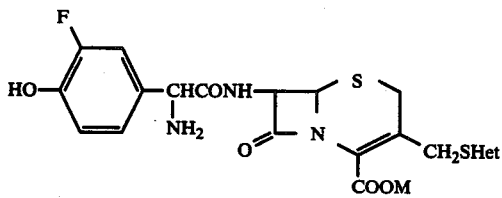

in which

Het is triazolyl, tetrazolyl, oxadiazolyl, thiazolyl, oxadiazolyl or thiadiazolyl, each of such groups being unsubstituted or substituted with two methyl groups or a straight chain lower alkyl group of from one to four carbon atoms and M is hydrogen or an alkali metal cation.

2. A compound as claimed in claim 1, being the compound 7-[α-amino-α-(3-fluoro- 4-hydroxyphenyl)acetamido]-3 -(5-methyl-1, 3,4-thiadiazol-2-ylthiomethyl)-3-cephem-4-carboxylic acid.

3. A compound as claimed in claim 1, being the compound 7-[α-amino-α-(3-fluoro-4-hydroxyphenyl)acetamido]-3-(1-methyl-1,2,3,4-tetrazol-5-ylthiomethyl)-3-cephem-4-carboxylic acid.

4. A compound as claimed in claim 1, being the compound 7-[α-amino-α-(3-fluoro-4-hydroxyphenyl)acetamido]-3-(1,2,3-triazol-4-ylthiomethyl)-3-cephem-4-carboxylic acid. d 5. An antibacterially effective pharmaceutical composition comprising a compound as claimed in claim 1 and a pharmaceutically acceptable carrier therefor.

6. An antibacterially effective pharmaceutical composition comprising a compound as claimed in claim 2 and a pharmaceutically acceptable carrier therefor.

7. An antibacterially effective pharmaceutical composition comprising a compound as claimed in claim 3 and a pharmaceutically acceptable carrier therefor.

8. An antibacterially effective pharmaceutical composition comprising a compound as claimed in claim 4 and a pharmaceutically acceptable carrier therefor.

9. A method of treating bacterial infections comprising orally administering to an infected or susceptible warm-blooded animal a pharmaceutical composition comprising an antibacterially effective but nontoxic dose from 100 to 500 mg. of a compound as claimed in claim 1 and a pharmaceutically acceptable carrier therefor.

10. A method as claimed in claim 9, in which the compound is 7-[α-amino-α-(3-fluoro-4-hydroxyphenyl)acetamido]-3-(1-methyl-1,2,3,4-tetrazol-5-ylthiomethyl)-3-cephem-4 carboxylic acid.

11. A method as claimed in claim 9, in which the compound is 7-[α-amino-α-(3-fluoro-4-hydroxyphenyl)acetamido]-3-(1,2,3-triazol-4-ylthiomethyl)-3-cephem-4-carboxylic acid.

* * * * *